(12) United States Patent
Cuzzato et al.

(10) Patent No.: US 6,479,717 B1
(45) Date of Patent: Nov. 12, 2002

(54) PROCESS FOR ELIMINATING CHLORINE FROM CHLOROFLUOROCARBONS

(75) Inventors: Paolo Cuzzato, Treviso (IT); Sergio Peron, Venice (IT)

(73) Assignee: Ausimont S.p.A., Milan (IT)

( * ) Notice: Subject to any disclaimer, the term of this patent is extended or adjusted under 35 U.S.C. 154(b) by 0 days.

(21) Appl. No.: 09/618,132

(22) Filed: Jul. 17, 2000

(30) Foreign Application Priority Data

Jul. 20, 1999 (IT) .......................................... MI99A1595

(51) Int. Cl.⁷ ................................................. C07C 19/08
(52) U.S. Cl. ...................................................... 570/163
(58) Field of Search ......................................... 570/163

(56) References Cited

U.S. PATENT DOCUMENTS 5,175,379 A * 12/1992 Cremer et al. .............. 570/163
5,345,014 A    9/1994 Cuzzato ...................... 570/163

FOREIGN PATENT DOCUMENTS

| EP | 0 356 892 A1 | 3/1990 |
| EP | 0 776 878 A2 | 6/1997 |
| FR | 1383927 | 11/1963 |
| WO | WO 95/16654 | 6/1995 |

* cited by examiner

Primary Examiner—Alan Siegel
(74) Attorney, Agent, or Firm—Arent Fox Kintner Plotkin & Kahn

(57) ABSTRACT

A gaseous process for eliminating chlorine atoms from a chlorofluorocarbon (CFC) of formula $C_nF_xCl_y$, wherein n is an integer from 1 to 3 and $x+y=2n+2$, wherein said compound is reacted with an hydrofluorocarbon of formula $C_{n'}F_{x'}H_{y'}$, wherein n', x', y' are as above defined, in the presence of a fluorination catalyst in solid phase at temperatures in the range 200° C.–400° C.

7 Claims, No Drawings

PROCESS FOR ELIMINATING CHLORINE FROM CHLOROFLUOROCARBONS

The present invention relates to a process for eliminating chlorine atoms from chlorofluorocarbons (CFCs) obtaining the corresponding fluorocarbons (FCs). The Montreal Treaty has banned the chlorofluorocarbon production, commercialization and dispersion in the atmosphere and therefore they cannot be industrially used any longer. These compounds can be disposed of by combustion in special incinerators, or can be transformed into harmless products for the ozone layer by using processes of the prior art. Specifically the processes are the following: the chlorofluorocarbon reaction with anhydrours hydrofluoric acid on catalyst, with formation of fluorocarbons (FCs), or the reaction with elementary hydrogen on platinum or palladium catalyst, which leads to the formation of the corresponding hydrofluorocarbons (HFCs).

Both these processes require specific plants since, as known, HF is highly toxic, hydrogen is flammable; the hydrochloric acid which develops in each of the two reactions is toxic and corrosive.

The need was therefore felt to have available processes in order to obtain the CFC conversion into industrially usable compounds.

An object of the present invention is a gaseous process for elimianting chlorine atoms from a chlorofluorocarbon (CFC) having formula $C_nF_xCl_y$, wherein n is an integer from 1 to 3 and x+y=2n+2, x being an integer in the range 1–7, preferably n is 1 or 2 and x is in the range 1–5, wherein said compound is reacted with a hydrofluorocarbon of formula $C_{n'}F_{x'}H_{y'}$ wherein n', x', y', equal to or different respectively from n, x, y, have the same meaning of n, x, y, in the presence of a fluorination catalyst in solid phase at temperatures in the range 200° C.–400° C., preferably 250° C.–320° C.

With the process of the invention it has surprisingly been found that a halogen exchange between CFC and HFC takes place, wherein CFC acquires fluorine and changes at last into FC while HFC acquires chlorine and changes into HCFC. There is no formation of other undesired by-products.

Starting from a CFC containing only one chlorine atom the corresponding FC is obtained. When the starting chlorofluorocarbon contains more than one chlorine atom, the process is repeated the necessary times until the corresponding fluorocarbon is obtained.

The HCFC compound obtained from HFC according to the reaction of the present invention can optionally be used as such, or recycled in the prior art processes for the HCFC/HFC production.

Therefore the process according to the present invention allows to obtain only compounds which have an industrial interest.

Said reaction is very selective and the amounts of organic by-products, and also of obtained hydrohalogenic acids (HF and/or HCl), are very reduced.

The fluorination catalyst of the invention is well known in the prior art, preferably a trivalent chromium compound, for example chromium oxide, optionally supported, can be mentioned. See the patents WO 95/16654 or U.S. Pat. No. 5,345,014.

The contact time with the catalyst, measured as the ratio between the catalyst volume and that of the gas flow at the working temperature and pressure, is not critical: long contact times lead to high conversions, while short contact times involve a higher flow of reacting gases, the catalyst volume being equal, and a lower conversion. There is therefore a balance, which is found by the skilled in the art, between the contact time and the conversion obtainable at each step, so as to optimize the reactor productivity. Generally the contact times range from 1 to 30 seconds.

The amount by moles of CFC and HFC in the mixture depends on the specific mixture under reaction.

CFCs are preferably selected from CFC 114 and CFC 115, HFCs from HFC 125 and 134a. The percent by moles of CFC 114 in the mixture HFC 125 ($CHF_2CF_3$) and CFC 114 ($CClF_2$—$CClF_2$) can for example range between 5% and 25%, while that of 134a in the mixture HFC 134a ($CF_3CH_2F$) and CFC 115 is at most of 15%.

The skilled in the art is easily capable to experimentally determine the preferred molar ratios between HFC and CFC.

The working pressure is not critical, but preferably one operates in the range 1–10 bar.

The reaction is carried out by flowing the CFC/HFC mixture, optionally diluted with an inert gas, through the catalyst in a fixed or fluidized bed. When the catalyst is in a fluidized bed the catalyst particles have sizes suitable for this process.

The fluorination catalyst can be supported, and the support is preferably aluminum fluoride $AlF_3$ obtainable by alumina fluorination and having a fluorine content not lower than 90%, preferably not lower than 95%, with respect to the stoichiometric.

Generally the aluminum fluoride is mainly constituted by gamma phase, as described in the patent FR 1,383,927, and has a surface area generally in the range 25–35 $m^2/g$. When the catalyst is used in a fluidized bed, the support must have the granulometry suitable for this kind of reactor, as it is well known to the skilled in the prior art.

When a trivalent chromium compound is used as fluorination catalyst, the chromium amount in the supported catalyst is in the range 5–15% by weight, preferably 10–15%, determined as metal amount with respect to the weight of the finished supported catalyst.

The supported catalyst is preferably prepared by impregnation of the support with an aqueous solution of a soluble salt.

The impregnation of the support can be carried out by any method known in the art, for example by the method known as "dry impregnation".

According to this method the impregnation is effected by pouring on the support, in sequence, aliquots of an impregnating solution, such that the total volume is not higher than the volume of the aluminum fluoride pores. The solution for the impregnation is prepared by dissolving in water the required amounts of the corresponding salts, preferably chlorides, of the desired metal, preferably trivalent chromium. The solution is poured in aliquots on the support, drying at 110° C. for some hours after each addition, to evaporate water from the support pores.

The unsupported catalyst is prepared by methods known in the art, for example by precipitation of a metal soluble salt, preferably of trivalent chromium as described in U.S. Pat. No. 5,345,014.

Before use the catalyst is activated by calcining for 4–8 hours in a current of inert gas, at the temperature of 400° C., and then treating it at 360° C. with anhydrous HF for a time comprised between 12 and 24 hours. The operation can be carried out in the reactor used for the process of the invention.

During the use the catalyst undergoes a slow deactivation, due to the deposit of organic substance; it can be regenerated by treating it with air at a temperature in the range 300° C.–400° C. for 4–8 hours and then with anhydrous HF at 360° C. for 12–24 hours.

It has been found that in the process of the invention the catalyst duration is very high.

Some examples are given for illustrative and not limitative purposes of the use possibilities of the invention.

EXAMPLE 1

In a tubular Inconel® 600 reactor having a 8 mm diameter, 2 g (about 1.5 ml) of the supported catalyst containing 10% by weight of chromium on aluminum fluoride support, having a granulometry suitable for the use in a fluidized bed are introduced. The catalyst is activated by treatment with nitrogen and then with anhydrous HF, as above described. At the temperature of 300° C. and at atmospheric pressure a mixture of CFC 115 (23.4 ml/min) and HFC 134a (2.8 ml/min) (about 12% by moles) is fed, obtaining a contact time of 1.8 s. The gases putflowing from the reactor are washed in water to absorb acidity traces, and analyzed by a gaschromatograph with thermoconductibility detector, equipped with a column formed by perfluoroethers on inert support (Fluorcol® or equivalent).

The results of the gaschromatographic analysis on the product mixture are reported hereinafter (% by moles):

FC 116: 6.23
HFC 134a: 1.36
CFC 115: 81.37
HCFC 133a: 10.91
others: 0.13

The conversion of 134a is 89%.

EXAMPLE 2

In the tubular reactor described in the previous Example 1, 2.9 g of the catalyst formed by chromium oxide in pellets (Engelhard® E-410T), activated as previously described, are fed. At the temperature of 260° C. and at atmospheric pressure a mixture of 8.7 ml/min of HFC-125 and 1.5 ml/min of CFC 114 is fed. The mixture before inlet into the reactor has the following composition by moles %: HFC-125: 88.7%; CFC-114: 11.3%. The contact time is 8,2 s. The gases outflowing from the reactor are treated and analyzed as indicated in Example 1. The results are reported hereinafter (% by moles):

FC 116: 0.07
HFC 125: 85.23
CFC 115: 3.46
HCFC 124: 2.72
HCFC 123: 0.80
CFC 114: 7.60
others: 0.12

The conversion of 114 is 32.5%. The selectivity in 115+116 is about 97% (calculated as 115+116 formed with respect to the converted 114).

EXAMPLE 3

In the same reactor and with the same catalyst of the previous Example, a test is carried out at 320° C., with a feeding of 18.5 ml/min of HFC-125 and 3.5 ml/min of CFC-114. The mixture contains 84% by moles of 125 and 16% by moles of 114. The contact time is 3.8 s. The gases outflowing from the reactor are treated and analyzed as indicated in Example 1.

The results are reported hereinafter (% by moles):

FC 116: 1.67
HFC 125: 77.14
CFC 115: 8.82
HCFC 124: 3.87
HCFC 123: 1.58
CFC 114: 4.77
others: 2.15

The conversion of 114 is about 70% and results much more high than at 260° C. and a not negligible amount of FC 116 forms. The selectivity in 115+116 is about 94%.

What is claimed is:

1. A gaseous process for eliminating chlorine atoms from a chlorofluorocarbon (CFC) of formula $C_nF_xCl_y$, wherein n is an integer from 1 to 3 and x+y=2n+2, x being an integer in the range 1–7, wherein said compound is reacted with an hydrofluorocarbon of formula $C_{n'}F_{x'}H_{y'}$, wherein n', x', y', equal to or different respectively from n, x, y, have the same meaning of n, x, y, in the presence of a catalyst consisting of trivalent chromium oxide supported on aluminum fluoride ($AlF_3$) obtainable by fluorination and having a fluorine content not lower than 90% with respect to the stoichiometric.

2. A process according to claim 1, wherein the contact time with the catalyst, measured as the ratio between the catalyst volume and that of the gas flow at the working temperature and pressure, is in the range 1–30 seconds.

3. A process according to claim 1, wherein CFCs are selected from CFC 114 and CFC 115 and HFCs from HFC 125 and 134a.

4. A process according to claim 3, wherein the percentage by moles of CFC 114 in the mixture HFC 125 and CFC 114 ranges from 5% to 25% by moles and that of 134a in the mixture HFC 134a and CFC 115 is at most 15%.

5. A process according to claim 1, wherein the catalyst is supported.

6. A process according to claim 5, wherein the fluorination catalyst is a trivalent chromium compound and the chromium amount in the supported catalyst is in the range 5–15% by weight, determined as metal amount with respect to the weight of the finished supported catalyst.

7. A process according to claim 6, wherein the chromium amount in the supported catalyst is in the range 10–15%, determined as metal amount with respect to the weight of the finished supported catalyst.

* * * * *